US006652280B2

(12) United States Patent
Cohen

(10) Patent No.: US 6,652,280 B2
(45) Date of Patent: *Nov. 25, 2003

(54) COMPOSITION AND METHOD FOR IMPROVING, ALTERING, AND TREATING TEETH

(76) Inventor: Morton Cohen, 8323 Twitchell Rd., Elkins Park, PA (US) 19027

( * ) Notice: Subject to any disclaimer, the term of this patent is extended or adjusted under 35 U.S.C. 154(b) by 0 days.

This patent is subject to a terminal disclaimer.

(21) Appl. No.: 09/791,204

(22) Filed: Feb. 22, 2001

(65) Prior Publication Data

US 2002/0006600 A1 Jan. 17, 2002

Related U.S. Application Data

(63) Continuation-in-part of application No. 09/370,325, filed on Aug. 9, 1999, now Pat. No. 6,210,163, which is a continuation-in-part of application No. 09/054,898, filed on Apr. 3, 1998, now Pat. No. 6,036,494.

(51) Int. Cl.$^7$ .................................................. A61C 5/00
(52) U.S. Cl. ..................................................... 433/217.1
(58) Field of Search ............................. 433/217.1, 215, 433/216; 434/49; 106/35

(56) References Cited

U.S. PATENT DOCUMENTS

| 3,932,938 A | 1/1976 | Mackta ........................... 32/15 |
| 4,032,627 A | 6/1977 | Suchan et al. ................. 424/54 |
| 4,097,994 A | 7/1978 | Reaville et al. ................. 32/15 |
| 4,141,144 A | 2/1979 | Lustgarten ...................... 32/15 |
| 4,259,069 A | 3/1981 | Lustig ......................... 433/144 |

(List continued on next page.)

FOREIGN PATENT DOCUMENTS

JP 07017822 A * 1/1995 ............ A61K/6/08

OTHER PUBLICATIONS

Klineberg I. and Earnshal R., "Physical Properties of Shellac Baseplate Materials." *Australian Dental Journal.* Oct., 1967, vol. 12, No. 5, pp. 468–475.
Azouka A., Hugget R., and Harrison A. "The Production of Shellac and its General and Dental Uses: A Review." *Journal of Oral Rehabilitation.* 1993, vol. 20, pp. 393–400.
Pharmascience, Inc. product insert and instructions for use entitled "DuraFlor".
Lee C., Pierpont H., and Strickler E. "The Effect of Bead Attachment Systems on Casting Patterns and Resultant Tensile Bond Strength of Composite Resin Veneer Cast Restorations." (The Journal of Prosthetic Dentistry), Nov., 1991., vol. 66, No. 5, pp. 623–630.
Komori A. H. and Ishikawa H., "Evaluation of a Resin–Reinforced Glass Ionomer Cement For Use as an Orthodontic Bonding Agent." (The Angle Orthodontist), 1997, vol. 67, No. 3, pp. 189–195.

Bayne S.C., Thompson J.Y., Swift Jr., E.J., Stamadtiades P., and Wilkerson M. "A Characterization of First–Generation Flowable Composites." (JADA), 1998, vol. 129, pp. 567–579.
Silverman E. and Cohen M. "Bonding of Orthodontic Attachments Using Ultaviolet Light Polymerized Adhesives." In Buonocore MG (Ed.), The Use of Adhesives in Dentistry. Charles C. Thomas, Publisher. Springfield, IL, 1975, pp. 372–388.
Silverman E., Cohen M. Demke. and Silverman M., "A New Light–Cured Ionomer Cement That Bond Brackets to Teeth Without Etching in the Presence of Saliva", (Amerian Assocation of Orthodon.), 1995, vol. 108, pp. 231–236.
GC Fuji I. Self Cure, REsin Reinforced Glass Ionomer Cement for Orthodontic Bonding. Brochure distributed by GC International Corp.
Bisco Aelite Seal Dual–Cured Pit and Fissure Sealant. Directions for Use and Material Safety Data Sheet. Brochure distributed by Bisco, Inc. Ithasca, IL 60143, Mar. 1996.
Mantrose Bradshaw Zinsser Group. Technical Information. "#4 REfined Pharmaceutical Glaze, NF in SDA 45/200 Alcohol." pp. 1–5.
Mantrose Bradshaw Zinsser Group. Literature regarding "Specially Denatured Alcohol." *U.S.I. Tank Cars at Tuscola, Illinois Plant*, pp. 23–25, 38 and 44.
Definition of "Lac" from http://www.life.uiuc.edu/plantbio/263/RESINS.html.
Definition of "shellac" from http://www.encyclopedia.com/articles/11792.html.
Lynn Bilton, Articles entitled "The Role of the Lac Bug in Recorded Sound" Noteworthy News Archives, Apr. 1988 from http://www.ubeaut.com.au/dewaxed.html.
A.F. Suter & Co. Ltd. Product Specification entitled "Common Solvents for Shellac" Revision No. 1.4, received Jun. 8, 1999 via facsmile.
Product sheet entitled "Dewaxed White Shellac" of 1988 by U–Beaut Enterprises.
The Colgate Oral Care Report entitled "The Efficacy of Fluoride Varnish", vol. 8, No. 3, 1998.

*Primary Examiner*—Kevin Shaver
*Assistant Examiner*—Melba Bumgarner
(74) *Attorney, Agent, or Firm*—Frank J. Bonini, Jr.; John F. A. Earley; Harding Earley Follmer & Frailey

(57) ABSTRACT

A composition and method for administering a treatment agent to a tooth, such as fluoride to improve the tooth's resistance to dental caries with a composition which can be selectively removed, the composition comprising a lac based compound with a treatment agent such as fluoride for applying to a tooth, and a method including selecting the color to be applied, preparing the colorized compound with the treatment agent to be applied to a tooth, exposing the tooth to be covered, applying the treatment containing a colorized compound to the enamel surface of the tooth, and allowing the compound to dry on the tooth, and selectively removing the compound from the tooth. Stencil apparatus can be used to create a design on the tooth using a covering compound.

27 Claims, No Drawings

U.S. PATENT DOCUMENTS

| | | | | |
|---|---|---|---|---|
| 4,384,058 | A | 5/1983 | Galante | 524/32 |
| 4,433,959 | A | 2/1984 | Faunce | 433/201 |
| 4,473,353 | A | 9/1984 | Greggs | 433/215 |
| 4,496,322 | A | 1/1985 | Sandham et al. | 433/217 |
| 4,512,743 | A | 4/1985 | Santucci et al. | 433/217 |
| 4,643,678 | A | 2/1987 | Hansen | |
| 4,682,950 | A | 7/1987 | Dragan | 433/90 |
| 4,776,939 | A | 10/1988 | Blasing et al. | |
| 4,822,279 | A | 4/1989 | Greggs | 433/202.1 |
| 4,992,049 | A | 2/1991 | Weissman | 433/215 |
| 4,997,367 | A | 3/1991 | Kassel | 433/39 |
| 5,094,615 | A | 3/1992 | Bailey | |
| 5,120,229 | A | 6/1992 | Moore et al. | 433/263 |
| 5,304,585 | A | 4/1994 | Bunker et al. | 523/116 |
| 5,326,264 | A | 7/1994 | Al Kasem | 433/224 |
| 5,360,340 | A | 11/1994 | Rheinberger et al. | 433/213 |
| 5,364,267 | A | 11/1994 | Fischer | 433/26 |
| 5,375,938 | A | 12/1994 | Bartlow | 403/202 |
| 5,403,577 | A | 4/1995 | Friedman | |
| 5,433,941 | A | 7/1995 | Patel | 424/50 |
| 5,456,905 | A | 10/1995 | Valenty | 424/61 |
| 5,512,611 | A | 4/1996 | Mitra | 523/116 |
| 5,520,725 | A | 5/1996 | Kato et al. | |
| 5,565,152 | A | 10/1996 | Oden et al. | 264/19 |
| 5,593,303 | A | 1/1997 | Cohen et al. | 433/9 |
| 5,639,447 | A | 6/1997 | Patel | 424/61 |
| 5,662,472 | A | 9/1997 | Grutzner | |
| 5,681,550 | A | 10/1997 | Rubino | 424/61 |
| 5,693,313 | A | 12/1997 | Shiraishi et al. | |
| 5,707,235 | A | 1/1998 | Knutson | 433/213 |
| 5,716,603 | A | 2/1998 | Chen et al. | 424/61 |
| 5,718,586 | A | 2/1998 | Sharp et al. | |
| 5,789,610 | A | 8/1998 | Bowen | |
| 5,814,682 | A | 9/1998 | Rusin et al. | 523/116 |
| 5,817,304 | A | 10/1998 | Mondet et al. | 424/78.03 |
| 5,882,635 | A | 3/1999 | Ramin et al. | 424/61 |
| 5,948,419 | A | 9/1999 | Bankert et al. | 424/401 |
| 6,030,222 | A | 2/2000 | Tarver | |
| 6,036,494 | A | 3/2000 | Cohen | |
| 6,210,163 | B1 | 4/2001 | Cohen | |

\* cited by examiner

COMPOSITION AND METHOD FOR IMPROVING, ALTERING, AND TREATING TEETH

CROSS-REFERENCE TO RELATED APPLICATIONS

This application is a continuation-in-part of U.S. application Ser. No. 09/370,325 filed on Aug. 9, 1999, now U.S. Pat. No. 6,210,163, which is a continuation-in-part of U.S. application Ser. No. 09/054,898, filed on Apr. 3, 1998, now U.S. Pat. No. 6,036,494.

BACKGROUND OF THE INVENTION

1. Field of the Invention

The present invention relates to the field of applying a composition to a tooth to alter the appearance thereof or provide a treatment to the tooth.

2. Brief Description of the Prior Art

Many procedures are done to improve the appearance of teeth. Teeth are filled to replace dentin and enamel invaded by bacteria, and can be capped to replicate a removed or abraded portion of a tooth.

The teeth of individuals widely vary in their appearance and shape. This is due to the genetic make-up of the individual, but can also be affected by age, and the degree of contact with various foods and medications, both those superficially contacting the teeth and from the internal effects of the medication. The teeth of some individuals exhibit a yellow appearance while those of others may be whiter. While aging is often considered a "natural" cause of tooth discoloration, other factors commonly attributed to tooth discoloration can include chemical exposure to tannins, which are found in red wines, and brewed beverages such as coffees and teas. Additional discoloring chemicals include those not naturally occurring in foods, but rather, manufactured or synthesized compounds, such as, for example, the compounds found in medications, like antibiotics, including tetracycline and other pharmaceuticals. The common practice of using doses of tetracycline to cure facial, acne blemishes has been known to contribute to the discoloration of teeth. Aside from these chemicals, even excess brushing can create discoloration by repeated contact with fluoride compounds commonly present in most toothpastes.

Many have attempted to confront the problem of tooth discoloration by proposing various solutions to whiten the teeth. One such method of tooth whitening involves the bonding of veneers onto the buccal or labial surfaces of a tooth. The veneer is usually constructed and applied by a dentist using dental bonding techniques to attach it to the tooth. Various veneers have been described in several U.S. Patents, see, e.g. U.S. Pat. No. 4,992,049 "Method for Applying a Veneer Facing to a Tooth"; U.S. Pat. No. 4,822,279 "Article for Cosmetic Restoration of Anterior Teeth" (which uses a glazed porcelain labial veneer); U.S. Pat. No. 4,682,950 "Device and Method of Bonding and Veneering Dental Material to a Tooth" (syringing composite material to a tooth surface which has been etched and coated with a bonding material); U.S. Pat. No. 4,473,353 "Method for Cosmetic Restoration of Anterior Teeth" (wherein a glazed porcelain veneer is bonded to a patient's tooth); and U.S. Pat. No. 4,433,959 "Composite Laminate Dental Veneer Containing Color Systems" (a veneer which is molded and then attached to the labial enamel surfaces of teeth).

Other attempts to whiten teeth are also known to include bleaching the teeth. Often the bleach is applied in the form of hydrogen peroxide, which can be obtained in drug stores by consumers. Because of the delicacy of applying hydrogen peroxide in one's mouth, some dentists carry out the procedure in their offices, using a stronger peroxide than can be purchased by the consumer. There are even pastes, sold over the counter, to the consumers which claim to whiten teeth. Often ordinary toothpastes make this claim, but increasingly appearing in the marketplace for purchase by consumers are pastes with the chemical compound sodium bicarbonate (baking soda), which may also contain peroxide. While chemical bleaching of teeth has been done to provide whiter-looking teeth, with its use there exists danger to the enamel of the teeth, especially if excessive exposure to chemical bleaches occurs. Further, chemical bleaching is understood in many cases to require multiple applications, and, hence, repeated use of the chemical. Even when applied by a dentist, precautions may be taken to prevent peroxide solution from contacting the patient's gums, which if otherwise allowed to come into contact therewith can be painful and cause damage to the gums. In cases of certain stains, bleaching may not be effective, and the stain may remain.

There are even procedures involving abrasion of the tooth enamel to present a smooth surface which is lighter in appearance than the stained surface removed. This has limitations as to the number of times it can be done.

Furthermore, abrading or bleaching teeth can have deleterious side effects, including, increased sensitivity of the treated tooth to temperature, i.e. especially when hot and cold foods and drinks are consumed. This effect may subside within time, but often the need to repeat bleaching procedures regularly, gives rise to a period of time within which the treated tooth can by hypersensitive.

There are some prior art whitening methods which require etching steps that are carried out with phosphoric acids. The use of phosphoric acid is generally done by a dentist under controlled conditions, for example, in the dentist's office. Caustic acid etchants have been recognized to be corrosive to the soft tissues of the mouth. For example, orthophosphoric acid, in some venues, must be transported pursuant to specified requirements and restrictions. In addition, the long term physiological effects of acid etching, which are generally unknown, have led practitioners to question certain acid etching uses in the field of dentistry. See e.g. M. G. Buonocore, "The Challenge of Bonding to Dentin", The Acid Etch Technique, L. M. Silverstone and I. L. Dogon, Eds., Proceedings of the International Symposium at St. Moritz, Switzerland, Dec. 16–18, 1974, North Central Publishing Co. (St. Paul, 1975). See also, U.S. Pat. No. 5,304,585, which raises these concerns, the complete disclosure of which is herein incorporated by reference; and see Akira Komori, and Haruo Ishikawa, "Evaluation of a Resin-Reinforced Glass Ionomer Cement for Use as an Orthodontic Bonding Agent," *The Angle Orthodontist*, Vol. 67 No. 3, 1997, the complete disclosure of which is herein incorporated by reference. Further attempts to whiten teeth are disclosed in U.S. Pat. No. 4,032,627 "Tooth Whitening Cosmetic Composition"; U.S. Pat. No. 4,097,994 "Dental Restorative Composition Containing Oligomeric Bis-GMA Resin and Michler's Ketone"; U.S. Pat. No. 4,141,144 "Dental Material and Method for Controlling Tooth Lustre"; and U.S. Pat. No. 4,512,743 "Method for Masking Discoloration on Teeth." U.S. Pat. Nos. 4,512,743 and 4,141,144, each use phosphoric acid application to the tooth in their treatments. U.S. Pat. No. 4,097,994 discloses a photocurable compound, which is used with a specific ultraviolet sensitizer and a peroxide catalyst to cure the compound. Furthermore, phosphoric acid etching generally disposes grooves in the tooth enamel in the nature of about 50 to 60 μm. This order of etching is visible and is noticed in the form of a dull tooth surface.

U.S. Pat. No. 4,032,627, referenced above, discloses the use of an alcohol-soluble composition to be applied to the surface of a tooth to whiten the tooth's appearance. This composition is suggested to be applied by the user. However, although this disclosure attempts to provide an extended wearing time for its compound, the composition is readily worn off by the abrasive action of food eaten after the compound is applied to the teeth, with certain, more abrasive, harder, foods causing faster wear of the composition from the tooth than other, softer foods.

The human body relies upon hydroxyapatite as the principal crystal for all calcified tissue. Hydroxyapatite is also found in teeth. Fluoride ion reacts with the hydroxyapatite in teeth. During the formation of teeth, generally in children, fluoride is known to improve the tooth's resistance to dental caries by reacting with the hydroxyapatite to form a more caries-resistant tooth. The reaction of hydroxyapatite with fluoride results in the formation of fluorapatite. The reaction equation is set forth below:

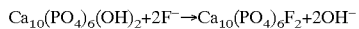

$$Ca_{10}(PO_4)_6(OH)_2 + 2F^- \rightarrow Ca_{10}(PO_4)_6F_2 + 2OH^-$$

While fluoride deposition may occur while teeth are being formed, before teeth appear in a child's mouth, low levels of fluoride in the tissue fluids are incorporated into the enamel crystals. Fluoride deposition continues in the enamel, and once the teeth erupt from the gums and become exposed in a child's mouth, the surface enamel can take up fluoride from sources such as drinking water (if fluoridated) and food.

Treatment agents such as fluoride, are applied to teeth in a medical office under the supervision of medical personnel such as a dentist. Fluoride can be dangerous if mishandled or ingested in excess quantities. Dental applications have comprised inserting a mouth piece in a patient's mouth and filling the mouth piece with a fluoride containing liquid which contacts the patient's teeth during the time in which the mouth piece remains inserted. This procedure is carried out by a dentist, is time consuming and can be uncomfortable for the patient. Also, teeth may not be fully covered due to the level which the mouthpiece can hold. While commercially available consumer products such as tooth pastes and rinses which contain fluoride have been provided for sale to the consumer directly, the amount of time that the fluoride containing composition is actually in contact with the teeth is minimal. This is purposefully done so as to avoid potentially harmful effects of fluoride poisoning. Although, fluoride is a known substance which is beneficial to teeth when topically applied to the tooth's surface in a known amount, fluoride can be toxic, and in certain doses, even fatal. A need therefore exists to provide fluoride in a beneficial amount where the fluoride application is controlled and the possibility of fluoride poisoning is reduced. It is desirable to provide a composition and method for covering a tooth, to appear white or colorized, which contains fluoride and can be selectively applied and removed by a user or non-medical personnel without harming the tooth or the individual wearer.

SUMMARY OF THE INVENTION

A novel composition and method for improving or altering the appearance of teeth, and for administering a treatment agent to teeth is provided by the present invention, where an individual, in his or her own home, a doctor's office, or even a non-medical office, can apply a compound to his or her teeth to alter the tooth by applying a design or indicia on the tooth or to apply a treatment agent to the tooth. The present method can be used to treat teeth, and can even be done in the presence of existing saliva which may be present on the tooth. The method provides a removable coating which can comprise a colorized or non-colorized coating which can be removed and replaced with other colorized coatings, or no further coatings, at the user's discretion. Expensive or dangerous drying apparatus are not required. Further, the composition of the present invention can be applied with or without an etching step, thereby avoiding the hazards inherent to use of caustic acid etchants, such as phosphoric and phosphonic acids. Moreover, when an individual's teeth, in accordance with the present method, require pre-treatment prior to application of the covering compound, the application of a naturally occurring substance can be used to facilitate adhesion. The substance can be lemon juice or lime juice, which unlike caustic acids, contains citric acid, which can be purchased by the consumer user of the covering compound which is to be applied by the present method. In a proposed alternate embodiment of the invention, polyacrylic acid is applied to the tooth surface prior to contact with the covering compound.

The present invention also provides a novel method for temporarily changing the color of a tooth on which the treatment is being applied. A palette system is provided wherein a user or wearer can select a color from one, or a combination of one or more, colorizing compounds. The selected or created color can then be incorporated with the other steps of the present method to provide a unique appearance to a tooth. The present method permits the user to mix his or her own colors or to select a color from one or more prepared provided colors. The color corresponds to the area of the tooth being treated.

A masking material, which preferably may comprise a film, may be applied onto the surface of a tooth to temporarily remain thereon so that the covering compound can be applied over the stencil to create a design or other indicia on the tooth.

The composition is a removable compound which contains a treatment agent and which can be applied to a tooth surface. Preferably, the composition includes a lac material, which is provided with a colorizing regulating compound or substance, in a solvent such as ethanol. Lac, the natural resinous substance excreted by an insect, Laccifer Lacca, has been used in dentistry mainly for the construction of special trays and bases for wax rims when recording jaw relationships. (See A. Azucca, R. Huggett, and A. Harrison, "The Production of Shellac and its General and Dental Uses: A review." *Journal of Oral Rehabilitation,* 1993, vol. 20, pp. 393–400, the complete disclosure of which is herein incorporated by reference; and I. Klineberg and R. Earnshaw, "Physical Properties of Shellac Baseplate Materials." Australian Dental Journal, October, 1967, vol. 12 no. 5, pp. 468–475.) Another use of shellac in dentistry includes treatment of a cavity with a hydrophilic shellac film placement of a polystyrene liner. (See M. Blixt and P. Coli, "The Influence of Lining Techniques on the Marginal Seals of Class II Composite Resin Restorations" *Quintessence International,* vol. 24, no. 3, 1993). Shellac has also been prepared and used in dentistry for the use of a bead adhesive for securing a composite resin veneer cast restoration. (See C. Lee, H. Pierpont, and E. Strickler, "The Effect of Bead Attachment Systems on Casting Patterns and Resultant Tensile Bond Strength of Composite Resin Veneer Cast Restorations", *The Journal of Prosthetic Dentistry*, November, 1991, vol. 66, no. 5, pp. 623–630.)

The treatment agent preferably comprises fluoride or a fluoride-containing compound which is mixed together with the lac resin. It is an object of the present invention to provide a novel composition and method for improving the appearance and character of teeth.

It is a further object of the present invention to provide a composition and a method that can be useful for delivering a treatment agent to the teeth to improve or alter their appearance.

It is a further object of the present invention to apply a treatment agent to teeth by covering stains or discolorations on a tooth by matching a colorized compound to an individual's teeth and applying the colorized compound containing the treatment agent on the surface of said stained or discolored teeth.

A further object of the present method is to change the appearance of a tooth by applying a colored or shaded composition containing a treatment agent to the tooth.

A further object of the present method is to match the appearance of a tooth to surrounding or adjacent teeth by applying a colored or shaded composition containing a treatment agent to the tooth.

A further object of the present invention is to coordinate colors of a tooth with other health and beauty aids by applying a method for colorizing a compound containing a treatment agent and applying it to a tooth.

Another object of the present invention is to provide a method for applying a compound containing a treatment agent to a tooth which can remain on the tooth during eating and other activity, and can be removed at the wearer's discretion, to leave the tooth as it appeared before the application of the compound.

A further object of the present invention is to provide a novel method of altering the appearance of a tooth which includes applying a compound to the tooth and selectively removing the compound from the tooth.

A further object of the present invention is to provide a method for altering the appearance of a tooth by contacting the tooth with a compound containing a treatment agent which can be repeated by the wearer, to change the appearance of a tooth, on a regular basis if the wearer desires, without having damaging effects on the tooth enamel.

Another object of the present invention is to provide a method which includes a color matching system wherein the user mixes components to colorize the composition containing a treatment agent to be applied to the tooth to the desired hue or color, which can be a tooth color or a non-tooth color.

It is another object of the present invention to accomplish the above objects by repeating application and removal of the compound containing a treatment agent on a tooth for different colors as the user determines and selects.

Another object of the present invention is to provide a tooth covering composition containing a treatment agent which can be selectively colorized, applied and removed by a user.

Another object of the present invention is to accomplish any of the above objects using a stencil to create a design or other indicia on a tooth.

Another object of the present invention is to provide a method and components for applying a design or other indicia to a tooth.

Another object of the present invention is to provide a compound which can be selectively removed from the tooth by a forced stream of water.

DETAILED DESCRIPTION OF THE INVENTION

The present invention provides a method for applying a treatment agent to teeth altering the appearance of teeth. The altered appearance can be the removal of stains or discoloration caused by disease, chemical exposure or aging, or can be the application of a color (i.e. red, blue, green, etc.) to the tooth at the same time during which the treatment agent is being applied. Generally the enamel of teeth is bound to tannins and other chemicals which remain on the enamel, in the form of a stain, which cannot be removed by brushing.

The present invention provides a composition which can be selectively applied to a tooth surface to provide a cosmetic alteration of the tooth, specifically, whitening or colorizing the tooth while delivering a treatment agent to the tooth. The compound, which is a lac based compound, preferably can be provided, or can be mixed by the user, to colorize the tooth a tooth colored shade, or one or more of a variety of colors (i.e. red, blue, green, etc.). The present method provides for the application of a lac based compound to the surface of a tooth to cover discolorings which are present on the tooth, or to provide a colorization of the tooth.

The treatment agent can comprise an element or a compound which has a benefit to the tooth. Fluoride is a preferred treatment agent is fluoride which can be delivered to the tooth through the contact of the lac based compound containing the treatment agent with the tooth. Fluoride has been known to have beneficial properties, particularly, in reducing the dental carries. A pigment compound is used to regulate the color of the tooth which is to be covered with the covering compound. For example, one pigment which can be used is titanium dioxide, which can yield a white or tooth colored shade. Other suitable pigments can be used, either separately, or combined to form desired shades.

The pigment can be used to indicate that the tooth has been covered with the fluoride containing compound. The coloring can also be provided to encourage children, who are particularly suitable for using fluoride, to utilize the composition to obtain the benefits of fluoride on their teeth.

The covering compound to be applied by the present method comprises an opaque material which masks the tooth surface. Preferably, the covering compound comprises a lac based compound.

The compound is prepared by dissolving a lac material into a solvent. The solvent used for the example below is ethanol (99% ethyl alcohol). The compound is preferably a liquid form which is fluid and can be painted on the surface of a tooth.

Shellac is a natural raw material, and is a complex resin comprising a material exuded from a scale insect. The insects which produce the lac are Laccifer lacca. One specific insect is a red lac bug (*tachardia lacca*), a member of the Coccidae group, commonly known as scale insects. Several trees of the Fabaceae (Butea, Cajanus, Acacia), Rhamnaceae (Zizyphus), Sapindaceae (Schleicheria) are the home to lac insects.

A reddish transparent material, referred to as "seed lac" is produced by the insects. Most harvesting of seed lac is done in India. The seed lac is generally adhered to sticks, which are collected. The lac deposits on the sticks are then stone ground and sifted and immersed in water where they are ground further by stomping or pulverizing. Unwanted materials, such as impurities rise to the surface where they can be easily collected for removal. The lac is then dried, and roasted in a mesh encapsulating material, after which it is strained through the mesh as a flowable, viscous substance to form a thin sheet. The sheet is permitted to cool and then broken down into flakes (sometimes referred to as shellac). Thereafter, the material is commercially processed or sold. It is these flakes that are utilized in the present invention. For example, the seed lac can be mixed with mineral spirits for use as a furniture polish or finish, pharmaceuticals, food industry.

A lac resin generally is a flake composition having a white, light brown, amber or yellowish color. Lac resins, although processed from a naturally occurring insect secretion, are generally commercially available.

A preferred lac resin for use in the present invention is the dewaxed orange flake type. This lac compound exhibits a light brown color and has the following characteristics:

| | |
|---|---|
| Acid No. | 65–80 |
| Ash | Max 0.3% |
| Melting Range | 65–85° C. |
| Moisture | Max 2.0% |
| Saponification No. | 190–230 |
| Wax | Max 0.2% |

Thermal Properties of Shellac

| | |
|---|---|
| Specific Heat @ 10° C.–40° C. | 0.36–0.38 cal/g/° C. |
| Thermal Conductivity @ 35° C. | 2.42 mW/cm/° C. |
| Coefficient of Cubical Expansion | |
| @ less than 45° C. | $2.73 \times 10^{-4}$/° C. |
| @ above 45° C. | $3.10 \times 10^{-4}$ cm/° C. |
| Polymerization Time @ 150° C. | 40–50 minutes |
| Flow or Fluidity by WESTINGHOUSE Method | 60–80 seconds |
| Softening Point | 55–65° C. |
| Melting Point | 65–75° C. |

The above data is for a lac resin sold as "Dewaxed Orange Flake Shellac" which was used in the examples that follow. Although the above data represents average properties for the lac used, it is understood that these can vary somewhat since the lac product is a natural secretion of an insect (before being processed into lac flakes).

Fluoride or a fluoride-containing compound may be added to the covering composition to be applied therewith to a tooth. Fluoride is added in a form which can be mixed with the lac resin composition. Fluoride is added in the form which can be mixed with the lac resin composition. For example, sodium fluoride can be used to provide the fluoride needed for the present composition. Fluoride is added so that the fluoride is present in the composition in an amount medically significant to provide a benefit to the tooth without harming the tooth. For example, fluoride present in the composition in preferred amounts of from about 0.1% to about 5% by weight can provide a benefit to the tooth. Lesser amounts may also provide a benefit to the tooth. In a preferred embodiment of the present invention, fluoride is added in amount of about 0.2% by weight. Preferably, the fluoride is added to obtain a concentration of about 0.2% fluoride by weight of the composition.

The covering compound with the fluoride is applied to the teeth in the present invention by painting it onto the tooth surface, preferably with a brush. This enables the composition to be evenly distributed to cover the entire tooth, and furthermore, without an excessive buildup or absence of material in one spot of the tooth. Alternately an aerosol suspension can be used to apply the covering compound to the tooth. For example, a small tube can be used through which the aerosol can be propelled for application onto the tooth. This facilitates even distribution of the covering compound on the tooth surface and avoidance of coverage on gums, skin and other non-tooth surfaces.

The present method also provides palette means for controlling the colorizing of the tooth. The palette means preferably comprises a plurality of pigments which are present in individual quantities for adding to the covering composition to be applied to the tooth. The palette means preferably is provided with a plurality of pigment means which contain tooth-colored pigments which can be matched to the individual user's tooth color. In addition, the palette means can contain colorful shades, such as, for example, blue, pink, pastel colors, or any other color which is supplied in the form of a pigment compound which can be mixed with the base covering compound and then be applied to the tooth by painting on the tooth.

The method can be carried out, for example, by providing a tray having a series of compartments containing tooth-colored pigments arranged in one row and a series of colorizing pigments in other rows. A larger compartment can be provided for the base compound or components. The compartments can have resealable covers which can be opened and closed by the user to remove a pigment or compound as needed. A mixing area can also be provided and can also have a cover.

Alternately, it is possible to apply the lac-based covering compound with the fluoride on the tooth, and then mix the color or pigment compound with the lac compound directly on the tooth. This may be done, for example, to facilitate approximating the shade of adjacent teeth.

In some circumstances, it may be desirable to etch a tooth surface to provide microscopic pits for facilitating adhesion of a compound to be applied thereto. Etching provides an increased surface area of the tooth. However, the present method also requires removability of the temporary tooth coating. In a preferred embodiment of the invention, the teeth of an individual can be pretreated with citric acid, of the same weakness of that concentration contained in lemon juice. This facilitates the adherence of the covering compound on the tooth's surface. The citric acid prepares the surface of the tooth to receive the compound which is to be painted on the tooth.

The method contemplates application of the tooth enhancing composition by an individual user or wearer having no special training or knowledge in dentistry. In this case, lemon juice can be used, since it will be easily obtained by the user. Alternately, citric acid solutions can be prepared or provided having the same general concentration as citric acid in lemon juice. By the use of the etching step, very small grooves or pits are formed on the tooth surface, which are approximately 5 to 10 $\mu$m or less. This enables the wearer of the compound to restore a treated tooth to its original appearance when desired by removing the covering compound. Another acid proposed for use with the compound of the present invention, for tooth preparation is polyacrylic acid.

Alternately, it is proposed that the covering compound, for example, can be prepared by taking a lac based composition, such as of the type described in Examples 1 or 2, comprising a 1 g. lac/10 ml ethanol solution, or in Examples 3 or 4, and providing an amount of a pigment compound which becomes the base pigment. To this pigmented base compound, the user can customize the color with the colorizing means, by selecting and combining pigment items and admixing the selected pigment items with the base compound. In addition, other elements, such as reflective means can be admixed as well to provide additional unique alteration of the tooth. For example, polymer particles, such as glitter, can be added to provide a sparkle effect to the tooth.

A colorizing pigment can be supplied in the form of a modified food starch or other color additive. The pigment can be supplied with the lac compound, or can be provided separately to be admixed by the user with the lac compound. The lac compound can be supplied to the user with a pigment to exhibit a tooth-colored shade, and can even be further mixed for colorization by the user.

The colorizing means of the present invention preferably can comprise a color additive, such as, for example, a dye, pigment or substance that can impart color when added or applied to the lac compound. Those particularly preferred include color additives of the type commonly used with a food, drug, cosmetic or in connection with the human body, especially color additives permitted for use in foods which are classified as "certifiable" or "exempt from certification." For example, the colorizing compound employed with the present method can include the exempt pigments, such as, for example, those listed below, derived from natural sources such as vegetables, minerals or animals, and man-made counterparts of natural derivatives. In addition, FDA certified pigments, such as, for example, the nine additives listed below can also be used.

Certified Color Additives

FD&C Blue No. 1 (Dye and Lake)
FD&C Blue No. 2 (Dye and Lake)
FD&C Green No. 3 (Dye and Lake)
FD&C Red No. 3 (Dye)
FD&C Red No. 40 (Dye and Lake)
FD&C Yellow No. 5 (Dye and Lake)
FD&C Yellow No. 6 (Dye and Lake)
Orange B
Citrus Red No. 2

Colors Exempt from Certification

Annatto extract
B-Apo-8'-carotenal
Beta-carotene
Beet powder
Canthaxanthin
Caramel color
Carrot oil
Cochineal extract (carmine)
Cottonseed flour, toasted partially defatted, cooked
Ferrous gluconate
Fruit juice
Grape color extract
Grape skin extract (enocianina)
Paprika
Paprika oleoresin
Riboflavin
Saffron
Titanium dioxide
Turmeric
Turmeric oleoresin
Vegetable juice The form of the additive for use in the present invention preferably includes dye form additives, but may also include lake forms which are compatible with the lac based covering composition. Water soluble dyes, provided in the form of powders, granules, liquids or other special-purpose forms can be used in accordance with the present method. Lakes, the water insoluble form of the dye, are generally used for coloring products which do not contain adequate moisture to dissolve the dyes. For example, if a suspension of color is to be used, a lake form additive can be employed. The color additive provided in the form of a lake may, for example, be used with other tooth appearance enhancing means such as glitter particles.

The present method includes the step of painting the compound on a tooth which is in its in vivo environment and an intermediary is not required. The naturally occurring saliva may be present on the tooth, and the compound can be applied with the saliva being present. Alternately, the method can include applying the compound to a tooth by spraying. For example, a compressed gas propellant, such as an aerosol, can be utilized to provide delivery of the covering compound to the tooth.

The selected compound is painted on the tooth and permitted to harden. The hardening of the compound occurs within about two to three minutes, wherein the alcohol dries or evaporates and the solubilized lac composition polymerizes. A layer is then formed by the compound covering the tooth surface on which it was applied, and becomes fixed on the tooth. The tooth thereby exhibits a new appearance, attributable to the compound.

The compound exhibits permanence and withstands normal buccal functions such as, for example, brushing, eating, chewing, contacting foods and beverages, and other functions carried out with one's teeth. During this time, the treatment agent can remain in contact with the tooth. The method applies a covering on the tooth which maintains a uniform appearance and is further resistant to staining. In addition, the covering protects the tooth against further staining and contact with bacteria and chemicals. The method applies a thin coating to the tooth which does not interrupt the user's normal mouth functions, and does not feel uncomfortable to a user.

The method further includes selectively removing the coating. The coating is removably provided on the tooth and can be removed from the tooth at the user's discretion. For example, if a user desires to change the color of the coated tooth, and, for example, apply a different color, then the first coating is removed to expose the original tooth surfaces again. A second or next coating can then be applied to the tooth to change the color. Removing preferably includes the step of using a pressurized stream of water, which can be done with a commercially available appliance, such as, for example, a WATER PIK®.

Alternately, it is proposed that a solvent may be used to remove the tooth coating. Preferably, the solvent comprises a composition which the user can readily obtain, or which can be supplied to the individual, non-medical personnel user. Furthermore, it is conceivable that compatible solvents can be used for removing the covering compound from a tooth by softening or dissolving the compound or its bonds. The solvent, for example, can be a material which may break up bonds between the lac polymerization and/or invade a bond formed between the compound and the tooth surface. The removal step wherein a solvent is used, can be accomplished by swabbing the solvent onto the tooth coating or around the edges thereof with a cotton swab. The coating is then loosened and can be more easily removed, or can even be dissolved.

Removal of the covering coating from the tooth then displays the original surface of the underlying tooth which had been covered by the coating.

Stenciling means is provided to facilitate making a design or other indicia on the tooth surface. The stenciling means includes a masking material, which preferably, may comprise a film which can be temporarily applied onto the surface of a tooth. The stenciling means can comprise a vinyl, adhesive-backed tape with a design or indicia cut into the tape. For example, the tape may be provided so that the user can customize the design by cutting his or her own design into the tape. Alternately, the tape may be provided with a plurality of precut designs which the user may select. The tape may be applied on a single tooth or may be applied as a strip to cover multiple teeth. The method of applying a design or other indicia to a tooth according to the present invention is carried out by selecting a design or indicia by choosing a particular tape or portion thereof. The method of applying the masking means can comprise activating the adhesive, for example, removing a removable peel-off release paper to expose the adhesive, and then applying the tape over the tooth with the design or indicia portion of the tape positioned over the area of the tooth on which the design is to be displayed. The vinyl tape contains a cut-out of the design such that when placed on the tooth, portions of the tooth are masked while other portions of the tooth are accessible. The accessible portions of the tooth are bound by the tape so that material, such as the covering compound of the present invention is applied over the vinyl tape, and mainly in the cut out area. The covering compound is permitted to dry, which can take up to about 1 minute, or perhaps longer, and the tape removed from the tooth to yield the design or indicia on the tooth. The excess covering compound which has been painted on the tape is removed with the tape.

The method may also comprise the step of cutting a design into the tape.

It will be understood that computer images may be transferred to thin films of vinyl or other material which can be cut and used as a mask. In addition, alternately, the method can include the steps of applying a first color covering compound to certain portions of the design, and a second colored covering compound to other areas. Or alternately, a covering compound having one color can be stenciled onto the tooth, and a covering compound of a second color is applied over the first colored compound. Additional color covering compounds may also be employed.

The indicia may comprise any design, image, letter, number or the like. The indicia can also be created by the user to comprise a unique design.

In another example, the tape is placed on a strip and designs are provided to be spaced apart so that multiple teeth can be painted at the same time.

The following is an example of the lac based covering compound and the method of the present invention, as carried out on human teeth in vivo. The dewaxed orange flake lac resin is used as indicated in Examples 1 and 2, below, to formulate a covering compound for cosmetically altering the appearance of a tooth, although it is conceivable that other lac resins, such as white lac, can also be used consistent with the scope of the present invention. While ethanol is described as a preferred solvent, it will be understood that an ethanol solution of less than 99% pure ethanol may be utilized, however, the drying times may be affected by the addition of alternate solvents.

Preferably, bleached lac resin may be used, such as, for example, refined bleached food grade (USP) dewaxed lac, NF. The bleached dewaxed lac resin was commercially prepared by dissolving bleached dewaxed lac resin in specially denatured alcohol 45/200 proof, to provide a clear solution containing approximately 35.3% plus or minus 1% (by weight) of solids and having a specific gravity of 0.911 plus or minus 0.01% g/cc typical. Therefore, refined bleached food grade dewaxed lac resin can be prepared by dissolving it in ethanol, or specially denatured alcohol such as SDA 45/200. Examples 3 and 4 relate to the bleached food grade dewaxed lac resin (obtained commercially from Mantrose-Haeuser Company) employed to prepare the covering compound. Fluoride can be provided as a salt, such as sodium fluoride.

EXAMPLE 1

An anterior tooth is prepared by retracting the individual's lip to expose the entire tooth, up to and including the upper gum line. The tooth was a front upper tooth. A quantity of 1 g. of lac resin (obtained commercially from A. F. Suter & Co. Ltd. as "Dewaxed Orange Flake Shellac" as discussed above), a dry light brown flake material was dissolved in 10 ml of grain alcohol (99% ethanol). A treatment agent is added to the compound. Fluoride is added in an amount to give about an 0.2% concentration by weight. A suitable amount of salt, such as sodium fluoride is added. A coloring agent was then added to tint the lac mixture to the desired shade. In this example, titanium dioxide powder (obtained commercially from Gamblin Dry Pigments, P. O. Box 625, Portland, Oreg. 97207) was admixed with the lac solution. The amount of titanium dioxide powder brought the color of the amber solution to a tooth colored shade, and the addition was an amount sufficient to arrive at the desired shade.

The covering compound with the fluoride was then applied onto the surface of the tooth. The covering compound dried within two minutes of its application by exposure to the air, the alcohol evaporating from the solution leaving a lac coating on the tooth. The result was an evenly-coated tooth, which presented an evenly-colored appearance. Any discoloration or uneven shading which was previously present on the tooth was no longer visible.

The tooth was used normally, for eating, drinking, and was brushed regularly for a four-day period, after which the coating on the tooth was easily removed by the application of a high pressure stream of water (supplied by the use of a WATER PIK®, an instrument which applies a pressurized stream of water onto the tooth, and which is commercially available to consumers). The coating was abraded and removed from the tooth with a WATER PIK®.

EXAMPLE 2

The above conditions were repeated, as reported for Example 1, above, for an upper front tooth. However, the tooth was first prepared by exposing the tooth to citric acid (applied in the form of lemon juice). The lemon juice was permitted to remain on the tooth for one minute, after which time, it was washed off of the tooth with a water rinse. The lac based covering compound with the treatment agent was then prepared and applied to the washed tooth, which was still wet, in accordance with the same procedure as in Example 1, above. This coating performed, and could be removed, in the same manner as the coating in Example 1, above.

EXAMPLE 3

An upper front tooth is prepared by retracting the individual's lip to expose the entire tooth, up to and including the upper gum line. The tooth is a front upper tooth. A quantity of about 0.10 mls of a lac resin solution (containing bleached food grade (USP) dewaxed lac resin solubilized in specially denatured alcohol formula 45/200 proof (SDA 45/200), obtained commercially from Mantrose-Haeuser Company, 1175 Post Road East, Westport, Conn. 06880, USA) is taken on a sable brush. The solution is a clear color. Fluoride is added to yield a 0.2% concentration in the solution.

A coloring agent is then added to tint the lac treatment solution to a desired shade. In this example, titanium dioxide powder (obtained commercially from Gamblin Dry Pigments, P. O. Box 625, Portland, Oreg. 92707) is admixed with the sample of lac solution taken on the brush. The sable brush deposits the lac solution sample onto a clean dish. An amount of pigment, equal to the size of a pinhead is added to the dish containing the lac solution sample, was admixed using the brush, until a uniformly pigmented covering compound results (i.e. wherein the pigment was uniformly distributed throughout the compound). The amount of titanium dioxide powder brings the color of the clear solution to a tooth colored shade, and the addition is an amount sufficient to arrive at the desired shade. The fluoride containing covering compound is brushed onto the tooth surface. The fluoride containing covering compound dried within minutes of its application. The tooth is used normally, for eating and drinking, and is brushed regularly during a twenty-four hour period, after which the coating on the tooth is removed by the application of a high pressure stream of water (supplied by the use of an instrument which applies a pressurized stream of water onto the tooth, and which is commercially available to consumers, such as, for example, a WATER PIK®). The coating is abraded and removed from the tooth with the WATER PIK®.

EXAMPLE 4

The above conditions were repeated, as reported for Example 3, above, for a front upper tooth. However, the tooth is first prepared by exposing the tooth to citric acid (applied in the form of lemon juice). The lemon juice is permitted to remain on the tooth for one minute, after which time, it is washed off of the tooth with a water rinse. The lac based covering compound is then prepared and applied to the washed tooth, which is still wet, in accordance with the same procedure as in Example 3, above. This coating performed, and is removable, in the same manner as the coating in Example 3, above.

EXAMPLE 5

The above conditions are repeated, as set forth in Example 3, above, for an upper front tooth. The covering compound containing a treatment agent is prepared by taking a quantity of about 0.10 mls of a lac resin solution containing bleached food grade (USP) dewaxed lac resin solubilized in specially denatured alcohol formula 45/200 proof (SDA) 45/200, (obtained commercially from Mantrose-Haeuser Company, 1175 Post Road East, Westport, Conn. 06880, USA) which is taken on a brush and mixed with a quantity of pigment in a dish. A fluoride containing compound is added to arrive at an 0.2% fluoride concentration by weight of the covering compound. The preparation of the covering compound is in accordance with the procedure identified above in Example 3, however, instead of titanium dioxide powder, a red pigment (red #22, sold commercially and obtained from Warner Jenkinson Co. Inc., 107 Wade Avenue, South Plainfield, N.J. 07080 as K-7008) is used. The compound is mixed and a red color resulted. The red covering compound with the treatment agent is applied to a tooth in the manner described in connection with Example 3. The red color when applied on the tooth indicates where the tooth is being treated. The tooth, having the red color from the compound applied to it, is used normally, for eating and drinking and is brushed regularly for a twenty-four hour period, after which the coating on the tooth is removed by the application of a high pressure stream of water (supplied by the use of an instrument which applies a pressurized stream of water onto the tooth and which is commercially available to consumers, such as, for example, a WATER PIK®). However, the tooth is first prepared by exposing the tooth to citric acid (applied in the form of lemon juice). The lemon juice is permitted to remain on the tooth for one minute, after which time, it is washed off of the tooth with a water rinse. The lac based covering compound is then prepared and applied to the washed tooth, which is still wet, in accordance with the same procedure as in Example 3, above. This coating performed, and could be removed, in the same manner as the coating in Example 3, above.

This example is also repeated using, in place of the red pigment, yellow #6 powder (FD&C 08006), and again using D & C yellow #10 (K-7059) (Warner-Jenkinson). However instead of a red color on the tooth, a yellow or orange color is obtained.

EXAMPLE 6

The covering compound is initially prepared, in accordance with Example 1, or by starting with the lac solution of Example 3. The covering compound is then further prepared by admixing with it a colorizing pigment. The colorizing pigment can be selected from color additives, including titanium dioxide and other pigments, vegetable dyes and the like. In this manner a variety of tooth-colored shades are possible, and can be matched to existing or surrounding teeth shades, by approximation with the addition of a pigment.

In this example, it is proposed that the covering compound is provided in a tooth colored shade to the user. The provided covering compound is then admixed with a selected pigment to provide a colorized compound. The colorized compound is applied to a tooth surface in the manner recited above in Examples 1 or 3, by painting it on the tooth surface. The compound is then permitted to dry by exposure to air, and selectively removed at the wearer's discretion.

EXAMPLE 7

The lac based covering compound is initially prepared in accordance with Examples 1 or 3. The covering compound is then further prepared by mixing a colorizing pigment. The colorizing pigment is selected from the pigments of the palette means. The palette means includes pigments comprising color additives, such as for example, titanium dioxide and other pigments, including vegetable dyes or food grade dyes. A containing means is used having pigment holding means for holding an array of pigments for selection by the user. The containing means also can have a mixing area wherein the selected pigments can be mixed with the lac based solution to arrive at the covering compound. The lac based covering compound is prepared by selecting from the palette means one or more pigment compound selections and mixing the selected pigment compound therewith with a solution containing lac resin and solvent.

The lac based covering compound can be provided in a tooth colored shade which can be further customized by the user with a selection from the pigment compounds. The tooth colored shade can preferably be provided by the addition of titanium dioxide or other suitable pigment, or by varying the types of lac used, or both.

The colorized covering compound is applied to a tooth surface in the manner recited above in Examples 1 or 3. The covering compound is then permitted to dry by exposure to air, and selectively removed at the wearer's discretion.

EXAMPLE 8

The compounds and methods described in Examples 1, 3, 5, 6 and 7, above, but further including an etching step. A weak acid is provided to etch very small microscopic pits onto the tooth surface. A citric acid solution is used. The citric acid solution preferably has the same concentration as lemon juice and, further, can be used in the form of lemon juice. The lemon juice is applied onto the tooth surface which is to receive the covering compound and allowed to remain on the tooth from about a few seconds to a few minutes. The lemon juice is then washed from the tooth with a water rinse. The tooth, still wet, is now ready to receive the covering compound. The covering compound is then applied by brushing onto the tooth surface to provide an evenly dispersed coating on the tooth. The compound is then permitted to dry by exposure to air, and selectively removed at the wearer's discretion.

EXAMPLE 9

The method is carried out as in Example 8, wherein the tooth preparing step includes etching the tooth with a polyacrylic acid solution (in place of the citric acid solution) by contacting the tooth with the polyacrylic acid solution and allowing the acid solution to remain on the tooth for a couple of minutes. The polyacrylic acid solution is then rinsed off of the tooth by applying a water rinse. Thereafter, the covering compound is applied.

EXAMPLE 10

The method is carried out as in any of Examples 1–9 above, wherein the covering compound is provided having a powdered component and a liquid component. The powdered component can contain the lac base and a pigment, which can be a tooth colored pigment or a non-tooth colored pigment. The powdered component can be provided in a plurality of pigmented shades for selection by the user. The powdered component is selected and mixed with a liquid component, which, for example, can contain ethanol, to form the lac based covering compound for application to an etched or non-etched tooth.

EXAMPLE 11

The method is carried out as in any of Examples 1 through 10 above, wherein a brightening agent is admixed with the covering compound, (or as in Example 10, with the powdered components). Preferably, the brightening agent can comprise pulverized fluoroaluminosilicate glass particles. The covering compound is applied and removed in the same manner. Furthermore, it is proposed that a Bis-GMA sealant or a glass ionomeric cement can be admixed with the lac based covering compound to provide a brightener. The fluoroaluminosilicate may be further added as well to the lac Bis-GMA and/or the lac glass ionomeric cement compound.

EXAMPLE 12

The method is carried out with the above examples except fluoride is added in an amount up to about 5% by weight of the composition.

In the case of a colored compound or non-tooth colored compound, preferably, there is some contrast between the tooth color and the composition being applied. The contrast facilitates identification of areas to which treatment has been applied, as well as those areas in need of treatment.

EXAMPLES 13–23

The above examples 1–11 are repeated, but without the addition of fluoride to the composition. The covering compound is applied to the tooth surface as described above.

EXAMPLES 24–46

The above examples 1–23 are repeated, however, prior to application of the compound, the tooth is masked with stenciling means which comprises a masking material. Where an etching step is included, the tooth may be etched prior to or after the application of a masking material to the tooth. A masking material having a design or indicia cut into the masking material forming an opening in the material is applied over the tooth surface. The covering compound is applied onto the opening of the masking material, and allowed to dry fully or until tacky. The masking material is them removed from the tooth, leaving behind the indicia or design comprising the covering compound. Excess covering compound which was applied on the masking material is removed with the masking material.

In each of the above examples, it is noted that no effort is made to dry the tooth, prior to applying the covering compound thereon.

In each of the above examples, it is noted that no effort is made to dry the tooth, prior to applying the covering compound thereon.

It will be apparent to those skilled in the art that various modifications can be made to the present invention without departing from the spirit and scope of the invention, and it is intended that the present invention cover modifications and variations which are within the scope of the appended claims and their equivalents.

What is claimed is:

1. A method for administering a treatment agent to the teeth, comprising the steps of:
 a) preparing the tooth by exposing the tooth so that the tooth to be treated is exposed;
 b) preparing a lac based covering compound containing a treatment agent to be applied onto the enamel surface of the tooth to be treated, including selecting a compound from a plurality of tooth colored compounds to match the shade of the adjacent or surrounding teeth in the individual's mouth;
 c) applying the covering compound prepared in step b to the tooth surface to be coated; and
 d) allowing the covering compound applied to the tooth to dry by exposing the tooth to air.

2. The method of claim 1, wherein the treatment agent comprises fluoride and wherein the method of administering a treatment agent comprises applying a fluoride treatment to a tooth.

3. The method of claim 1, wherein the step of preparing a lac based covering compound containing a treatment agent includes selecting a color from one or more non-tooth colored compounds and mixing said non-tooth-colored compound with said lac based covering compound to provide an overall non-tooth colored appearance.

4. The method of claim 3, further including the step of providing palette means, said palette means including a plurality of pigmented compounds, and selecting one or more of said pigmented compounds from said palette means and mixing said selected one or more pigmented compounds with said the lac based covering compound of step b) before applying said lac based covering compound to said tooth.

5. The method of claim 3, further including the step of providing a food grade dye as the colorizing compound and blending said food grade dye with said lac based covering compound to provide a colorized covering compound.

6. The method of claim 1, further including the step of selectively removing the lac based covering compound applied to the tooth.

7. The method of claim 6, wherein the step of selectively removing the lac based covering compound from the tooth includes contacting the compound with solvent.

8. The method of claim 6, wherein the step of selectively removing the lac based covering compound containing a treatment agent includes applying to the tooth surface containing the lac based covering compound a forced stream of water.

9. The method of claim 1, wherein colorizing means is provided containing a plurality of pigments, and wherein the method further includes the steps of selecting from colorizing means at least one pigment, and mixing said pigment selected from said colorizing means with said lac based covering compound to be applied to the tooth.

10. The method of claim 9, further including the step of mixing a reflecting material into said lac based covering compound to be applied to said tooth.

11. The method of claim 1, wherein the step of preparing a lac based covering compound includes providing a lac resin and dissolving said lac resin in an ethanol solution.

12. The method of claim 1, wherein the step of preparing the lac based covering compound includes admixing pulverized fluoroaluminosilicate glass particles.

13. The method of claim 1, wherein the step of preparing a tooth further includes the steps of providing a weak acid solution and contacting the tooth surface with the weak acid solution.

14. The method of claim 13, wherein the step of contacting the tooth with a weak acid solution, includes etching the tooth with an acid selected from the group of citric acid and polyacrylic acid.

15. The method of claim 14, further including the step of providing as an etchant lemon juice.

16. The method of claim 1, wherein the step of preparing a tooth further includes the step of etching microscopic pits which are less than about 5.0 $\mu$m in the tooth surface with an etchant.

17. The method of claim 1, wherein the step of preparing a lac based covering compound further includes selecting a food grade dye and blending said dye with said covering compound to provide a colored covering on said tooth.

18. A method for treating teeth with fluoride, comprising the steps of:
a) preparing a tooth by exposing the tooth so that the tooth surface to be treated is exposed;
b) providing palette means containing a plurality of tooth-colored shaded pigment compounds, including the step of providing a container means for holding the pigment compounds and providing a mixing area;
c) selecting from said palette means one or more of said pigment compounds contained in the container means to match the shade of adjacent or surrounding teeth in an individual's mouth;
d) preparing a lac based covering compound containing fluoride to be applied onto the enamel surface of the tooth to be altered by placing said lac based covering compound in said mixing area of said container means and adding to said lac based covering compound from said container means a pigment compound from said palette means;
e) mixing said covering compound with said pigment compound;
f) applying the lac based covering compound prepared in step (e) to the tooth surface to be coated; and
g) drying the covering compound applied to the tooth in step (f) by exposing the covered tooth to air.

19. The method of claim 18, wherein the step of preparing a tooth further comprises the steps of:
a) providing a weak acid solution;
b) etching the tooth by contacting the tooth with a weak acidic solution to provide small microscopic pits in the enamel surface of said tooth; and
c) rinsing the weak acid solution off of the tooth with water.

20. A method for treating teeth with fluoride wherein a removable coating is applied directly on the tooth and cured on the tooth surface, including providing a lac based covering compound with fluoride which comprises a lac compound and a solvent, providing means for storing the lac based covering compound and associated means for storing one or more colorizing pigment compounds, wherein the lac based covering compound is provided as the covering compound with another compound selected from the group consisting of Bis-GMA sealants and glass ionomeric cements, preparing the tooth by leaving it wet and exposing the tooth surface which is to be cosmetically altered, the user having the ability to select from the associated means one or more colorizing pigment compounds and mix said selected one or more colorizing pigment compounds with the lac compound and solvent to form a pigmented covering compound, applying the pigmented covering compound to cover the surface of the tooth to be altered, drying the pigmented covering compound by exposure to air, wherein the pigmented covering compound remains on the tooth and wherein the pigmented covering compound is removable from the tooth at the user's discretion.

21. The method of claim 1, wherein the step of preparing a lac based covering compound further comprises providing said lac based covering compound in a fluidic suspension for delivery by spraying, and wherein the step of applying the covering compound to the tooth surface comprises the step of spraying the covering compound on the tooth surface.

22. A covering composition for application to a tooth for administering a treatment agent to the tooth, said covering composition comprising dewaxed orange flake lac resin solubilized in an ethanol solution at a concentration of 1 g. per 10 ml of ethanol, a pigment, and a treatment agent, wherein the treatment agent comprises fluoride.

23. The composition of claim 22, wherein the treatment agent comprises sodium fluoride.

24. A composition for cosmetically altering the appearance of teeth to whiten or colorize the teeth by applying said composition to a tooth surface, said composition comprising:
a) a lac resin;
b) a solvent for dissolving said lac resin; and
c) fluoride; and d) a pigment;

e) wherein said solvent comprises ethanol;

f) wherein the concentration of said lac resin is approximately 1 g./10 ml ethanol.

25. A composition for cosmetically altering the appearance of teeth to whiten or colorize the teeth by applying said composition to a tooth surface, said composition comprising:

a) a lac resin;

b) a solvent for dissolving said lac resin;

c) fluoride;

d) a pigment;

e) a brightening agent; and f) wherein said solvent comprises ethanol; and g) wherein said brightening agent comprises finely divided fluoroaluminosilicate compound, and wherein the composition is selectively removable.

26. A composition for cosmetically altering the appearance of teeth to whiten or colorize the teeth by applying said composition to a tooth surface, said composition comprising:

a) a lac resin;

b) a solvent for dissolving said lac resin;

c) fluoride; and d) a pigment;

e) wherein said ethanol comprises ethanol f) wherein said lac resin comprises refined bleached food grade dewaxed lac; and g) wherein said ethanol comprises specially denatured alcohol, formula 45/200 proof.

27. The composition of claim 26, wherein the concentration of said lac resin is approximately 34 to 37% by weight.

* * * * *